(12) United States Patent
Zhang et al.

(10) Patent No.: US 11,835,436 B2
(45) Date of Patent: Dec. 5, 2023

(54) SPECIMEN PREPARATION METHOD FOR ELIMINATING MEMBRANE PENETRATION EFFECT ON HIGHLY-WEATHERED ROCK

(71) Applicant: Institute of Rock and Soil Mechanics, Chinese Academy of Sciences, Wuhan (CN)

(72) Inventors: Xianwei Zhang, Wuhan (CN); Xinyu Liu, Wuhan (CN); Chao Ma, Wuhan (CN); Jijun Du, Wuhan (CN); Ruiduo Li, Wuhan (CN); Cheng Chen, Wuhan (CN)

(73) Assignee: Institute of Rock and Soil Mechanics, Chinese Academy of Sciences, Wuhan (CN)

( * ) Notice: Subject to any disclaimer, the term of this patent is extended or adjusted under 35 U.S.C. 154(b) by 492 days.

(21) Appl. No.: 17/198,156

(22) Filed: Mar. 10, 2021

(65) Prior Publication Data

US 2021/0190649 A1   Jun. 24, 2021

Related U.S. Application Data

(63) Continuation of application No. PCT/CN2019/077577, filed on Mar. 9, 2019.

(30) Foreign Application Priority Data

Nov. 21, 2018  (CN) .......................... 201811393379.1

(51) Int. Cl.
*G01N 1/28* (2006.01)
*G01N 1/30* (2006.01)
*G01N 33/24* (2006.01)

(52) U.S. Cl.
CPC ............. *G01N 1/286* (2013.01); *G01N 33/24* (2013.01); *G01N 2001/2873* (2013.01); *G01N 2001/305* (2013.01); *G01N 2203/0256* (2013.01)

(58) Field of Classification Search
CPC ............. G01N 1/286; G01N 2001/305; G01N 2001/2873; E21B 25/08; E21B 49/02; E21B 49/06
See application file for complete search history.

(56) References Cited

U.S. PATENT DOCUMENTS 4,393,699 A   7/1983 Seiler, Jr.

FOREIGN PATENT DOCUMENTS

| CN | 102507904 A | 6/2012 |
|---|---|---|
| CN | 102628767 A | 8/2012 |

(Continued)

OTHER PUBLICATIONS

Yan, Wai Man "Experimental Study and Constitutive Modelling of Re-compacted Completely Decomposed Granite" Thesis, The Hong Kong University of Science and Technology, Jan. 2003. (Year: 2003).*

(Continued)

*Primary Examiner* — Paul M. West
(74) *Attorney, Agent, or Firm* — MEI & MARK LLP; Manni Li

(57) ABSTRACT

A specimen preparation method for eliminating a membrane penetration effect on a highly-weathered rock, wherein the method makes an originally uneven surface of a specimen smooth using a cured liquid latex as a filler, thereby eliminating a membrane penetration effect on a highly-weathered rock, and comprises the following specimen preparation steps: specimen cutting, pit filling, surface smoothing, specimen shaping and specimen loading.

4 Claims, 11 Drawing Sheets

(56) References Cited

FOREIGN PATENT DOCUMENTS

| | | | |
|---|---|---|---|
| CN | 103175949 A | | 6/2013 |
| CN | 204882551 U | * | 12/2015 |
| CN | 108414343 A | | 8/2018 |

OTHER PUBLICATIONS

Evans, M.D. "Liquefaction and dynamic properties of gravelly soils" Transactions on the Built Environment, vol. 3, 1993. (Year: 1993).*

Zhou, Jingxing et al., "Extreme Correction Method of Rubber Film's Impact in Dynamic Triaxial Test,"Journal of Hydraulic Engineering, No. 5, pp. 9-16 (May 31, 1986).

Wang, Kunyao et al., "Preliminary Study on Membrane Penetration Effects in Coarse-Grained Soil Specimens," Dam Observation and Geotechnical Tests, vol. 24, No. 4, pp. 45-46, and 49 (Aug. 20, 2000).

Wang, Y. H., et al., "Laboratory Studies of Two Common Saprolitic Soils in Hong Kong," Journal of Geotechnical and Geoenvironmental Engineering, 132(7), pp. 923-930 (2006).

Zhu, Sizhe et al., "Triaxial Test Principle and Application," Beijing, China Electric Power Press, pp. 101-105 (2003).

Lu, Xiaoping, et al., "Study on the Influence of End Restraints of Triaxial Specimens of Coarse-grained Soil," Chinese Journal of Geotechnical Engineering, 39 (Supplement 1): pp. 236240 (2007).

"Standard for Soil Test Method," (GB/T50123-1999), National Standard in China, pp. 90-106 (1999).

ASTM D412-16e1, "Standard Test Methods for Vulcanized Rubber and Thermoplastic Elastomers—Tension," ASTM International, West Conshohocken, PA, 2016, www.astm.org. (2016).

* cited by examiner

SPECIMEN PREPARATION METHOD FOR ELIMINATING MEMBRANE PENETRATION EFFECT ON HIGHLY-WEATHERED ROCK

CROSS-REFERENCE TO RELATED APPLICATIONS

The subject application is a continuation of PCT/CN2019/077577 filed on Mar. 9, 2019, which claims priority on Chinese Application No. CN201811393379.1 filed on Nov. 21, 2018 in China. The contents and subject matter of the PCT international application and the Chinese priority application are incorporated herein by reference.

BACKGROUND OF THE INVENTION

Technical Field

The invention relates to preparation methods of triaxial specimens for soil tests, and particularly relates to a specimen preparation method for eliminating a membrane penetration effect on a highly-weathered rock.

Description of Related Art

Highly-weathered rocks, as special soil formed by weathering, have mechanical properties different from those of sandy soil and clayey soil formed by deposition. At present, triaxial shear texts carried out indoors are important means for acquiring mechanical indicators of such soil, and constitutive model parameters adopted by some designs also depend on test results of the triaxial shear texts. However, residual sand grains of parent rocks may penetrate into clay matrixes, thus making the surface of cylindrical specimens adopted during the tests uneven or resulting in large pits in the surface. When a conventional triaxial drained or undrained shear test is carried out, a membrane will penetrate into these pits or large voids with the application of a confining pressure (Wang, Y. H., et al., "Laboratory studies of two common saprolitic soils in Hong Kong," Journal of Geotechnical and Geoenvironmental Engineering, 2006, 132(7): 923-930), and this phenomenon is referred to as a membrane penetration effect. Many studies, (Zhu, Sizhe et al., "Triaxial Test Principle and Application," Beijing, China Electric Power Press (2003)), (Wang, Kunyao et al., "Preliminary Study on the Influence of Membrane Penetration on Coarse-grained Soil Specimens," Dam Observation and Soil Engineering Test, 2000, 24(4): 45-46) have shown that the membrane penetration effect will cause large errors of measured water discharge. For example, when the triaxial drained shear test is carried out on some undisturbed specimens containing large particles (Lu, Xiaoping, et al., "Study on the Influence of End Restraints of Triaxial Specimens of Coarse-grained Soil," Chinese Journal of Geotechnical Engineering, 2017, 39 (Supplement 1): 236-240), a membrane will penetrate into voids in the lateral surface of a specimen under the membrane penetration effect and squeeze water out of the voids, thus increasing the volumetric water discharge of the specimen and resulting in a higher tested volumetric water discharge. In view of this, the influence of the membrane penetration effect on test results is a factor that must be taken into consideration.

Traditional studies on the membrane penetration effect during triaxial tests are generally based on two ideas: one is to measure the membrane penetration by some presumptive theories or tests and then to correct test results, and the other one is to directly reduce or eliminate the influence of membrane penetration during the specimen preparation process by some measures. Generally, the first method adopts a relatively complicated theory, involves a large amount of calculation, and may causes large membrane penetration errors, which has been introduced in detail in the soil mechanics treatise Triaxial Test Principle and Application. So, the second method is generally adopted to directly eliminate the membrane penetration. As for the second method directly eliminating the membrane penetration, for example, by attaching copper sheets or stainless steel sheets to the surface of a specimen, it is pointed out in the study of Lu Xiaoping, et al., (see Lu Xiaoping et al., "Study on the influence of End Restraints on Triaxial Specimens of Coarse-grained Soil," Chinese Journal of Geotechnical Engineering, 2017, 39 (Supplement 1): 236-240) that such a method increases the radial size of the specimen and reduces the volume deformation of soil, but there will be still partial membrane penetration under a high confining pressure due to the large granularity of soil particles, so the existing method for directly eliminating the membrane penetration has many disadvantages. In addition, most studies on the influence of the membrane penetration effect aim at coarse-grained soil. As for highly-weathered rocks containing a large quantity of clay particles or powder particles, triaxial specimens of the highly-weathered rocks are different from triaxial specimens of the coarse-grained soil containing coarse particles or sand particles. It is impossible to completely fill in pits in the uneven surface of the specimens of the highly-weathered rocks through conventional membrane penetration elimination methods, such as by attaching copper sheets or stainless steel sheets to the surface of the specimens. Thus, existing specimen preparation methods for eliminating a membrane penetration effect cannot be applied to highly weather rocks, either.

In view of the particularities of triaxial tests of the highly-weathered rocks and the disadvantageous influences of the membrane penetration effect, there is an urgent need for a specimen preparation method for eliminating a membrane penetration effect on a highly-weathered rock, which will improve the test precision of triaxial test results and will be of great significance for accurately determining construction and design control indicators.

BRIEF SUMMARY OF THE INVENTION

The objective of the invention is to overcome the defects of the prior art by providing a specimen preparation method for eliminating a membrane penetration effect on a highly-weathered rock, which is easy to operate and can effectively solve the problem of inaccurate test results caused by the membrane penetration effect on the highly-weathered rock when an indoor triaxial shear test is carried out at present.

To fulfill the above objective, the following technical solution is adopted: a specimen preparation method for eliminating a membrane penetration effect on a highly-weathered rock fills pits in the surface of a specimen with a liquid latex to make the surface of the specimen smooth so as to eliminate a membrane penetration effect during a test, and comprises the following steps:

(1) Specimen cutting: a soil specimen is taken out of a soil specimen tube or a packaging bag, a soil layer on the surface of the soil specimen is removed by cutting to obtain a standard cylindrical triaxial specimen, and the diameter of the specimen is tested with a slide caliper and is recorded as $d_1$;

(2) Pit filling: wet filter paper is laid on upper and lower surfaces of the specimen, the liquid latex is smeared on a peripheral surface of the specimen for packaging and is leveled with a cutter to make the peripheral surface of the specimen smooth, and finally, the packaged specimen is placed in a moisture preservation vat and stands until the liquid latex on the peripheral surface of the specimen is cured;

(3) Surface smoothing: the specimen processed in Step (2) is placed into a membrane sleeve and is integrally cured with the membrane sleeve, wherein an inner surface of the membrane sleeve is coated with the liquid latex, and the thickness of the membrane sleeve is $d_0$;

(4) Specimen shaping: the specimen processed in Step (3) is instantly placed in a triaxial confining pressure chamber after porous stones are placed in an upper portion and a lower portion of the specimen respectively, a confining pressure is applied to press the liquid latex into the specimen, and the specimen stands until the liquid latex is cured; and (5) Specimen loading: the confining pressure is released, the membrane sleeve is removed, the outer diameter $d_2$ of the specimen is measured with the slide caliper, and a specimen meeting $d_2/d_1 < 1.01$ is loaded for a triaxial shear test.

According to the specimen preparation method for eliminating a membrane penetration effect on a highly-weathered rock, in Step (1), the diameter of the specimen is 50.00 mm, the height of the specimen is 100.0 mm, the soil specimen contains 15.0 wt % of gravel particles, 50.0 wt % of sand particles and 35.0 wt % of clay particles.

Furthermore, between Step (2) and Step (3), the specimen preparation method comprises membrane sleeve preparation, which includes the following steps: J01, a membrane tube is disposed around a membrane, then two ends of the membrane are turned outwards to be attached to the outside of the membrane tube, and the portions, located outside the membrane tube, of the membrane are banded with rubber bands; J02: a pointed end of a plastic suction bulb is inserted into a suction hole of the membrane tube, and the plastic suction bulb is pressed to exhaust air between the membrane and the membrane tube; and J03: the liquid latex is dipped with a finger wearing a latex glove and is then smeared in the membrane, wherein the average thickness of the liquid latex smeared in the membrane is 0.1 mm.

Furthermore, in Step (4), the confining pressure applied is 10 kPa, and the liquid latex is pressed into voids of particles on the surface of the specimen.

Furthermore, during pit filling in Step (2), the liquid latex stands in the moisture preservation vat for 5 h to be cured.

Furthermore, during surface smoothing in Step (3), the thickness of the liquid latex smeared in the membrane is 0.1 mm.

Furthermore, during specimen shaping in Step (4), the liquid latex stands in the confining pressure chamber for 5 h to be cured.

The principle of the technical solution of the specimen preparation method for eliminating a membrane penetration effect on a highly-weathered rock of the invention is as follows: large pits in local parts of the surface of the specimen are filled with the liquid latex at first, then the liquid latex is smeared on the originally uneven surface of specimen to make the surface smooth, and the cured liquid latex is a soft filler that will not apply a constraint force to the specimen or exert an influence on the radial diameter of the specimen, so that an obvious membrane penetration effect on the highly-weathered rock is completely eliminated, which makes an obtained triaxial shear test result true, reliable and precise.

The specimen preparation method for eliminating a membrane penetration effect on a highly-weathered rock provided by the invention has the following advantages and beneficial effects:

① Costs are low. Test equipment and materials used are all common instruments and consumables in laboratories, so that the costs are low.

② Operations are simple. Assembly is easy, test steps are simple and feasible, operations by professional technicians are not needed, and manpower and material resources are saved.

③ Test materials are non-toxic and harmless. The liquid latex adopted is prepared from natural latex and is harmless to the health of testers.

④ The specimen preparation cycle is short, the preparation time of one triaxial specimen is not over 12 h, mass specimen preparation can be realized, and the test cycle is shortened significantly.

⑤ In the invention, the originally uneven surface of the specimen is smoothed, so that the problem of water seepage of the specimen caused when protruding quartz particles on the surface of the specimen penetrate through the membrane under high pressure is effectively avoided.

⑥ The highly-weathered rock differs from coarse-grained soil in that it contains clay particles, so uneven small pits are more likely to be formed in the surface of the cylindrical specimen; the existing specimen preparation methods for the coarse-grained soil cannot fully fill in these small pits and thus cannot completely eliminate the membrane penetration effect. The invention solves this problem by a processing technique combining pit filling and surface smoothing.

Figure 1:
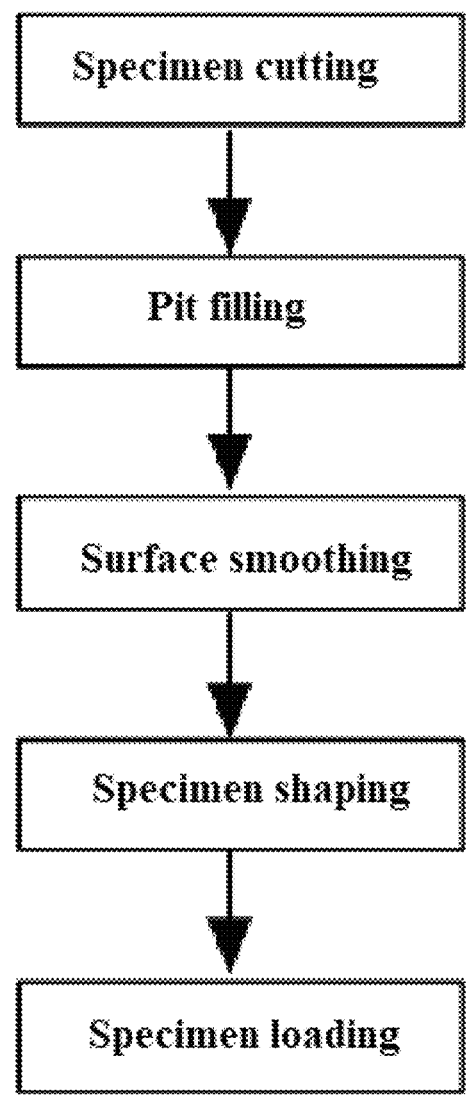
FIG. 1 is a flow diagram of the operation process of a specimen preparation method for eliminating a membrane penetration effect on a highly-weathered rock according to the invention.

Reference numerals in the drawings are used to refer to the following structures: $1_a$—first filter paper; $1b$—second filter paper; 2—clay particle; 3—sand particle; 4—liquid latex; 5—membrane; 6—membrane tube; $6b$—second outer cylinder; 7—suction hole; 8—plastic rubber suction bulb; $9a$—first rubber band; $9b$—second rubber band; 10—cylindrical specimen.

DETAILED DESCRIPTION OF THE INVENTION

To make the objective, contents and advantages of the invention clearer, a specimen preparation method for eliminating a membrane penetration effect on a highly-weathered rock provided by the examples of the invention will be explained below in further detail in conjunction with the accompanying drawings.

Example 1

In the example, a test material is highly-weathered granite in Xiamen and contains 15.0 wt % of gravel particles, 50.0 wt % of sand particles and 35.0 wt % of clay particles, a specimen is a standard triaxial specimen (with a diameter of 50.0 mm and a height of 100.0 mm) and undisturbed, the thickness $d_0$ of a membrane adopted is 0.3 mm, and a confining pressure for consolidation is 500 kPa.

As shown in FIG. 1, the specimen preparation method for eliminating a membrane penetration effect on a highly-weathered rock comprises the following steps:

(1) Specimen Cutting

Figure 2:
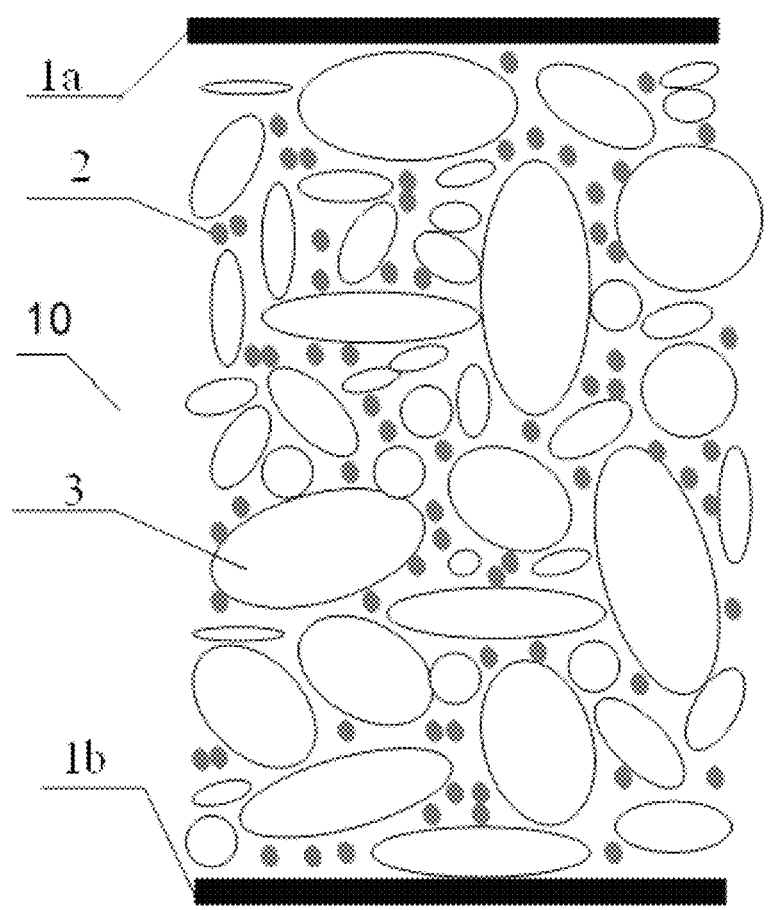
FIG. 2 is a schematic diagram of a cylindrical specimen of a highly-weathered rock after cutting.

A soil column with sizes a bit larger than the sizes (diameter 50.0 mm, height 100.0 mm) of a triaxial specimen is obtained; the soil column is cut with a soil cutter at first until the height of the specimen reaches 102.0 mm; then, the side face of the specimen is cut with a wire saw until the specimen is cut into a cylinder with a diameter of 50.0 mm; and finally, the specimen is cut with the wire saw until the height of the specimen reaches 100.0 mm, so that a cylindrical specimen 10 with standard sizes is obtained, as shown in FIG. 2; and after cutting, the diameter $d_1$ of the specimen 10 is tested with a slide caliper.

(2) Pit Filling

Figure 3:
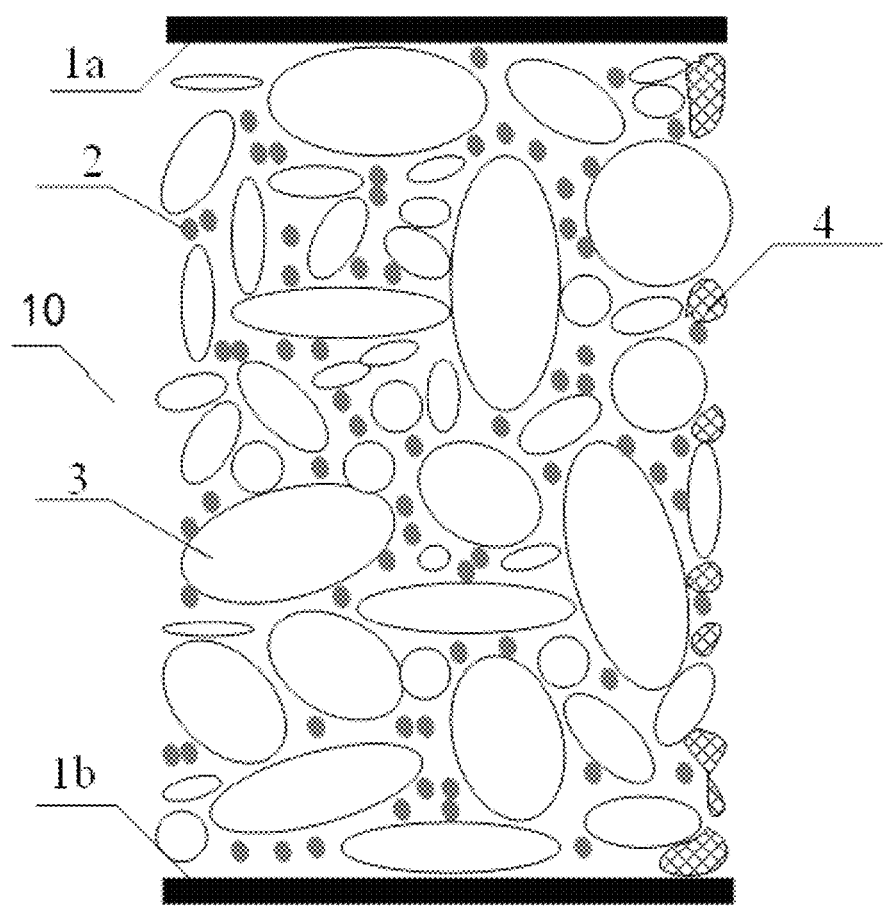
FIG. 3 is a schematic diagram of the cylindrical specimen of the highly-weathered rock after pit filling.

Wet first filter paper $1a$ and wet second filter paper $1b$ are pasted on the upper surface and the lower surface of the specimen 10 respectively; then the first filter paper $1a$, the specimen 10 and the second filter paper $1b$ are sequentially placed on a horizontal test stand; a liquid latex 4 to be filled in pits in the surface of the specimen is scrapped with a small blade, the liquid latex 4 adopted in the example is No.C1204 produced by Woodland Scenics, is up to the quality standard of American Society for Testing and Materials (abbreviated as ASTM), is non-toxic, and has a relatively density of 0.98, a viscosity of 15 mPa·s and a pH of 7.1, and the liquid latex 4 is filled in pits between the clay particles 2 and the sand particles 3; after that, the liquid latex 4 is carefully leveled with the soil cutter to make the specimen 10 as smooth as possible; when all the pits are filled with the liquid latex 4, the first filter paper $1a$, the specimen 10 and the second filter paper $1b$ are placed in a moisture preservation vat and stand for 5 h until the liquid latex 4 is cured, and the cylindrical specimen 10 obtained after pit filing is shown in FIG. 3.

(3) Surface Smoothening

Figure 4:
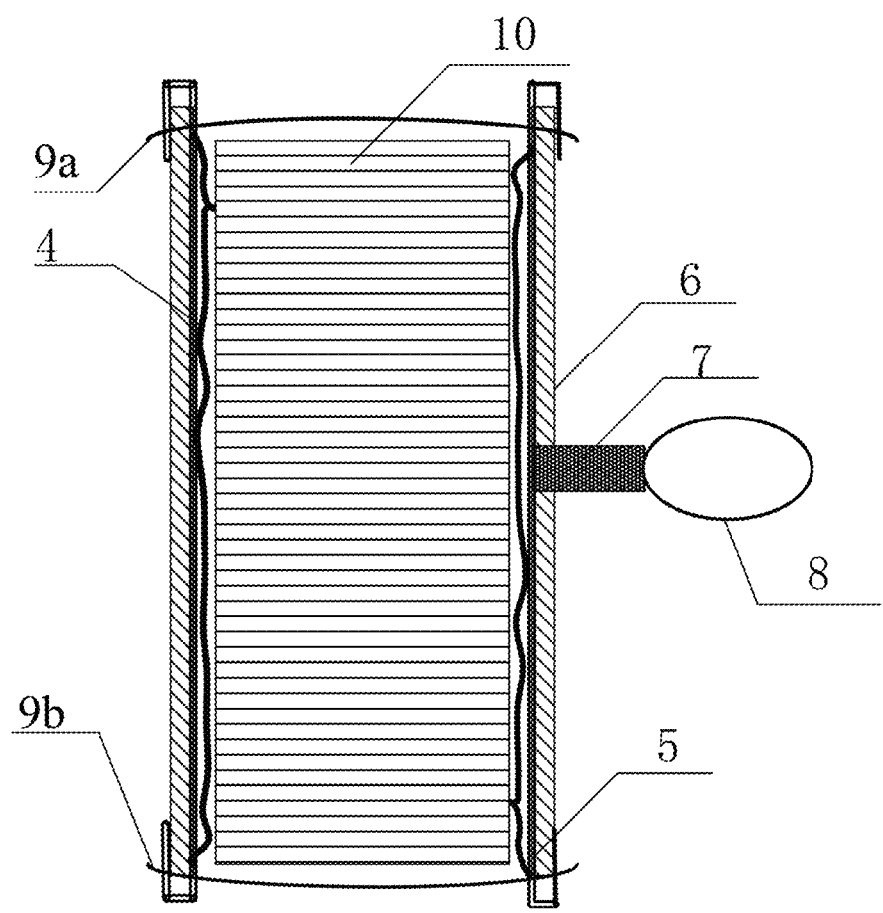
FIG. 4 is a schematic diagram of surface smoothing of the specimen preparation method for eliminating a membrane penetration effect on a highly-weathered rock according to the invention.

As shown in FIG. 4, a membrane sleeve is prepared: a membrane 5 is placed into a membrane tube 6, two ends of the membrane 5 are turned outwards to make the membrane 5 closely attached to the outside of the membrane tube 6, the membrane 5 and upper and lower portions of the membrane tube 6 are banded with a first rubber band $9a$ and a second rubber band $9b$, a pointed end of a plastic suction bulb 8 is inserted into a suction hole 7 and is pressed by hand to exhaust air between the membrane 5 and the membrane tube 6 to attach the membrane 5 to the membrane tube 6, and the liquid latex 4 is dipped with a finger wearing a latex glove and is then smeared in the membrane 5 to obtain the membrane sleeve, wherein the average thickness of the liquid latex smeared in the membrane is 0.1 mm. The specimen 10 is taken out of the moisture preservation vat and is placed in the membrane sleeve, and the specimen 10 obtained after surface smoothing is shown in FIG. 4.

(4) Specimen Shaping

The plastic suction bulb 8, the first rubber band $9a$, the second rubber band $9b$ and the membrane tube 6 are removed sequentially, a porous stone is placed in each of upper and lower portions of the specimen 10 wrapped with the membrane 5, then the specimen 10 is instantly placed in a triaxial confining pressure chamber, a 10 kPa confining pressure is applied to press the liquid latex 4 into voids of particles on the surface of the specimen until the voids are full of the liquid latex, and the specimen 10 stands for 5 h under the 10 kPa confining pressure to cure the liquid latex 4.

(5) Specimen Loading

The confining pressure is released; the specimen 10 wrapped with the membrane 5 is taken out, and the outer diameter $d_2$ of the specimen 10 is measured with the slide caliper, wherein $d_2$ is equal to the sum of $d_0$, $d_1$ and the thickness of the cured liquid latex 4. The influence of the thickness of the membrane having the liquid latex 4 cured thereon on the triaxial test is evaluated by calculation according to the following formula:

$$M=d_2/d_1.$$

If M is less than 1.01, it will be regarded that the thickness of the membrane having the liquid latex 4 cured thereon will not exert an additional constraint force on the specimen, and the prepared specimen will be loaded in terms of Standard for Soil Test Method (GB/T50123-1999) for the triaxial test; or, if M is greater than 1.01, it will be regarded that the thickness of the membrane having the liquid latex 4 cured thereon may exert an additional constraint force on the specimen, which will increase the intensity of the specimen; and in this case, specimen preparation and loading need to be carried out again according to Step (1)-Step (4) until M is less than 1.01, and then the triaxial shear test will be carried out.

M obtained by the specimen preparation method for eliminating a membrane penetration effect on a highly-weathered rock according to the invention is 1.008.

The triaxial shear test is carried out in terms of Standard for Soil Test Method (GB/T50123-1999), a TSZ30-2.0 bench triaxial instrument produced by Nanjing Soil Instrument Co., Ltd. is used as test equipment, and the triaxial shear test comprises the following specific steps:

① Specimen loading: the specimen is loaded according to Step (1)-Step (5);

② Installation of the confining chamber: a piston at the top of the confining chamber is lifted, the pressure chamber is lowered, the position is aligned to the center of the specimen, base connecting nuts are uniformly tightened, pure water is injected into the pressure chamber, an exhaust hole is tightened when water overflows from the exhaust hole in the top of the pressure chamber, and the piston is aligned to a forcemeter and the top of the specimen;

③ Installation of the forcemeter: a clutch is adjusted to a rough adjustment gear, and a rough adjustment hand wheel is rotated; when a specimen cap and the piston are close to the forcemeter, the clutch is adjusted to a fine adjustment gear, and a fine adjustment hand wheel is used to make the specimen cap and the piston contact with the forcemeter; a deformation indicator is installed, and the forcemeter and the deformation indicator are adjusted to zero;

④ Application of a consolidation pressure: a drain valve is closed, a pressure valve around is opened, and a 500 kPa consolidation pressure is applied;

⑤ Shearing: a motor is started and the clutch is closed to start shearing, and the shear strain rate is controlled to 0.5% per minute; and when a reading on the forcemeter reaches a peak value, shearing should be continuously carried out until the axial strain reaches 20%;

⑥ End of the test: when the test ends, the motor is stopped, the pressure valve around is closed, the clutch is opened and is adjusted to the rough adjustment gear, and the rough adjustment hand wheel is rotated to lower the pressure chamber, the exhaust hole is opened, water in the pressure chamber is drained, the pressure chamber cover is disassembled, and the specimen is unloaded.

Example 2

To better verify the reliability and practicability of the specimen preparation method for eliminating a membrane penetration effect on a highly-weathered rock of the invention, a test material containing particles different from those in Example 1 is selected, and the test material in Example 2 is highly-weathered granite in Shenzhen and contains 10.0 wt % of gravel particles, 45.0 wt % of sand particles and 45.0 wt % of clay particles. In addition, to check the influence of the sizes of the specimen, the thickness of the membrane and the confining pressure for consolidation on the specimen preparation method, the sizes of the specimen and the thickness of the membrane are different from those in Example 1, wherein the diameter of the specimen is 38.0 mm, the height of the specimen is 80.0 mm, the thickness $d_0$ of the membrane is 0.2 mm, and the confining pressure for consolidation is 500 kPa.

As shown in FIG. 1, the specimen preparation method for eliminating a membrane penetration effect on a highly-weathered rock comprises the following steps:

(1) Specimen Cutting

A soil column with sizes a bit larger than the sizes (diameter 38.0 mm, height 80.0 mm) of a triaxial specimen is obtained; the soil column is cut with a soil cutter at first until the height of the specimen reaches 82.0 mm; then, the side face of the specimen is cut with a wire saw until the specimen is cut into a cylinder with a diameter of 40.0 mm; and finally, the specimen is cut with the wire saw until the height of the specimen reaches 80.0 mm, so that a cylindrical specimen 10 with standard sizes is obtained, as shown in FIG. 2; and after cutting, the diameter $d_1$ of the specimen 10 is tested with a slide caliper.

(2) Pit Filling

Wet first filter paper 1a and wet second filter paper 1b are pasted on the upper surface and the lower surface of the specimen 10 respectively; then the first filter paper 1a, the specimen 10 and the second filter paper 1b are sequentially placed on a horizontal test stand; a liquid latex 4 to be filled in pits in the surface of the specimen is scrapped with a small blade, and the liquid latex 4 adopted in Example 1 is No.C1204 produced by Woodland Scenics and is filled in pits between the clay particles 2 and the sand particles 3; after that, the liquid latex 4 is carefully leveled with the soil cutter to make the specimen 10 as smooth as possible; when all the pits are filled with the liquid latex 4, the first filter paper 1a, the specimen 10 and the second filter paper 1b are placed in a moisture preservation vat and stand for 5 h until the liquid latex 4 is cured, and the cylindrical specimen 10 obtained after pit filing is shown in FIG. 3.

(3) Surface Smoothing

As shown in FIG. 4, a membrane sleeve is prepared: a membrane 5 is placed into a membrane tube 6, two ends of the membrane 5 are turned outwards to make the membrane 5 closely attached to the outside of the membrane tube 6, the membrane 5 and upper and lower portions of the membrane tube 6 are banded with a first rubber band 9a and a second rubber band 9b, a pointed end of a plastic suction bulb 8 is inserted into a suction hole 7 and is pressed by hand to exhaust air between the membrane 5 and the membrane tube 6 to attach the membrane 5 to the membrane tube 6, and the liquid latex 4 is dipped with a finger wearing a latex glove and is then smeared in the membrane 5 to obtain the membrane sleeve, wherein the average thickness of the liquid latex smeared in the membrane is 0.1 mm. The specimen 10 is taken out of the moisture preservation vat and is placed in the membrane sleeve, and the specimen 10 obtained after surface smoothing is shown in FIG. 4.

(4) Specimen Shaping

The plastic suction bulb 8, the first rubber band 9a, the second rubber band 9b and the membrane tube 6 are removed sequentially, a porous stone is placed in each of upper and lower portions of the specimen 10 wrapped with the membrane 5, then the specimen 10 is instantly placed into a triaxial confining pressure chamber, a 10 kPa confining pressure is applied to press the liquid latex 4 into voids of particles on the surface of the specimen until the voids are full of the liquid latex, and the specimen 10 stands for 5 h under the 10 kPa confining pressure to cure the liquid latex 4.

(5) Specimen Loading

The confining pressure is released; the specimen 10 wrapped with the membrane 5 is taken out, and the outer diameter $d_2$ of the specimen 10 is measured with the slide caliper, wherein $d_2$ is equal to the sum of $d_0$, $d_1$ and the thickness of the cured liquid latex 4. The influence of the thickness of the membrane having the liquid latex 4 cured thereon on the triaxial test is evaluated by calculation according to the following formula:

$$M = d_2/d_1.$$

If M is less than 1.01, it will be regarded that the thickness of the membrane having the liquid latex 4 cured thereon will not exert an additional constraint force on the specimen, and the prepared specimen will be loaded in terms of Standard for Soil Test Method (GB/T50123-1999) for the triaxial test; or, if M is greater than 1.01, it will be regarded that the thickness of the membrane having the liquid latex 4 cured thereon may exert an additional constraint force on the specimen, which will increase the intensity of the specimen; and in this case, specimen preparation and loading need to be carried out again according to Step (1)-Step (4) until M is less than 1.01, and then the triaxial shear test will be carried out.

M obtained by the specimen preparation method for eliminating a membrane penetration effect on a highly-weathered rock according to the invention is 1.007.

The triaxial shear test is carried out in terms of Standard for Soil Test Method (GB/T50123-1999), a TSZ30-2.0 bench triaxial instrument produced by Nanjing Soil Instrument Co., Ltd. is used as test equipment, and the specific steps of the test are the same as those in Example 1.

Comparative Test 1:

Due to the fact that the curing time of the liquid latex 4 has a great influence on the triaxial specimen preparation method, which will indirectly influence the accuracy of test results, and that the thickness of the liquid latex 5 smeared in the membrane 5 in Step (3) in Example 1 and Example 2 also has a great influence on the test results, this comparative test adopts a test material and condition the same as those in Example 2 and a different curing time and thickness of the liquid latex 4.

As shown in FIG. 1, the specimen preparation method for eliminating a membrane penetration effect on a highly-weathered rock comprises the following steps:

(1) Specimen Cutting

A soil column with sizes a bit larger than the sizes (diameter 38.0 mm, height 80.0 mm) of a triaxial specimen is obtained; the soil column is cut with a soil cutter at first until the height of the specimen reaches 82.0 mm; then, the side face of the specimen is cut with a wire saw until the specimen is cut into a cylinder with a diameter of 40.0 mm; and finally, the specimen is cut with the wire saw until the height of the specimen reaches 80.0 mm, so that a cylindrical specimen 10 with standard sizes is obtained, as shown in FIG. 2; and after cutting, the diameter $d_1$ of the specimen 10 is tested with a slide caliper.

(2) Pit Filling

Wet first filter paper 1a and wet second filter paper 1b are pasted on the upper surface and the lower surface of the specimen 10 respectively; then the first filter paper 1a, the specimen 10 and the second filter paper 1b are sequentially placed on a horizontal test stand; a liquid latex 4 to be filled in pits in the surface of the specimen is scrapped with a small blade, and the liquid latex 4 adopted in Example 1 is No.C1204 produced by Woodland Scenics and is filled in pits between the clay particles 2 and the sand particles 3; after that, the liquid latex 4 is carefully leveled with the soil cutter to make the specimen 10 as smooth as possible; when all the pits are filled with the liquid latex 4, the first filter paper 1a, the specimen 10 and the second filter paper 1b are placed in a moisture preservation vat and stand for 3 h until the liquid latex 4 is cured, and the cylindrical specimen 10 obtained after pit filing is shown in FIG. 3.

(3) Surface Smoothing

As shown in FIG. 4, a membrane sleeve is prepared: a membrane 5 is placed into a membrane tube 6, two ends of the membrane 5 are turned outwards to make the membrane 5 closely attached to the outside of the membrane tube 6, the membrane 5 and upper and lower portions of the membrane tube 6 are banded with a first rubber band 9a and a second rubber band 9b, a pointed end of a plastic suction bulb 8 is inserted into a suction hole 7 and is pressed by hand to exhaust air between the membrane 5 and the membrane tube 6 so as to attach the membrane 5 to the membrane tube 6, and the liquid latex 4 is dipped with a finger wearing a latex glove and is then smeared in the membrane 5 to obtain the membrane sleeve, wherein the average thickness of the smeared liquid latex is 0.05 mm. The specimen 10 is taken out of the moisture preservation vat and is placed in the membrane sleeve, and the specimen 10 obtained after surface smoothing is shown in FIG. 4.

(4) Specimen Shaping

The plastic suction bulb 8, the first rubber band 9a, the second rubber band 9b and the membrane tube 6 are removed sequentially, a porous stone is placed in each of upper and lower portions of the specimen 10 wrapped with the membrane 5, then the specimen 10 is instantly placed into a triaxial confining pressure chamber, a 10 kPa confining pressure is applied to press the liquid latex 4 into voids of particles on the surface of the specimen until the voids are full of the liquid latex 4, and the specimen 10 stands for 5 h under the 10 kPa confining pressure to cure the liquid latex 4.

(5) Specimen Loading

The confining pressure is released; the specimen 10 wrapped with the membrane 5 is taken out, and the outer diameter $d_2$ of the specimen 10 is measured with the slide caliper, wherein $d_2$ is equal to the sum of $d_0$, $d_1$ and the thickness of the cured liquid latex 4. The influence of the thickness of the membrane having the liquid latex 4 cured thereon on the triaxial test is evaluated by calculation according to the following formula:

$$M=d_2/d_1.$$

If M is less than 1.01, it will be regarded that the thickness of the membrane having the liquid latex 4 cured thereon will not exert an additional constraint force on the specimen, and the prepared specimen will be loaded in terms of Standard for Soil Test Method (GB/T50123-1999) for the triaxial test; or, if M is greater than 1.01, it will be regarded that the thickness of the membrane having the liquid latex 4 cured thereon may exert an additional constraint force on the specimen, which will increase the intensity of the specimen; and in this case, specimen preparation and loading need to be carried out again according to Step (1)-Step (4) until M is less than 1.01, and then the triaxial shear test will be carried out.

M obtained by the specimen preparation method for eliminating a membrane penetration effect on a highly-weathered rock according to the invention is 1.006.

The triaxial shear test is carried out in terms of Standard for Soil Test Method (GB/T50123-1999), a TSZ30-2.0 bench triaxial instrument produced by Nanjing Soil Instrument Co., Ltd. is used as test equipment, and the specific steps of the test are the same as those in Example 1 and Example 2.

Comparative Test 2:

The test material in Example 1 is adopted: highly-weathered granite in Xiamen containing 15.0 wt % of gravel particles, 50.0 wt % of sand particles and 35.0 wt % of clay particles; the specimen is a standard triaxial specimen (with a diameter of 50.0 mm and a height of 100.0 mm) and undisturbed, the thickness $d_0$ of a membrane adopted is 0.3 mm, and a confining pressure for consolidation is 500 kPa.

To compare the advantages and disadvantages of the technical solution of the invention and existing specimen preparation methods for weakening an membrane penetration effect on an undisturbed specimen, the specimen preparation method put forward in the literature (Lu, Xiaoping et al., "Study on the influence of End Restraints on Triaxial Specimens of Coarse-grained Soil," Chinese Journal of Geotechnical Engineering, 2017, 39 (Supplement 1): 236-240) fills a specimen with a stainless steel sheet or a copper sheet in the specimen preparation process and comprises the following steps: a specimen cap is lubricated by placing a polished stainless steel sheet or copper sheet with a hole in the middle (for draining) at two ends of the specimen and placing a latex membrane (0.4 mm thick) with one side coated with lubricating oil (silicon grease) between the stainless steel sheet or the copper sheet and the specimen, wherein the periphery of the latex membrane is cut in the radial direction and the side coated with the lubricating oil is attached to the stainless steel sheet; and the specimen loading method put forward by Lu Xiaoping adopts a triaxial test process and steps completely the same as those in Example 1.

Figure 5:
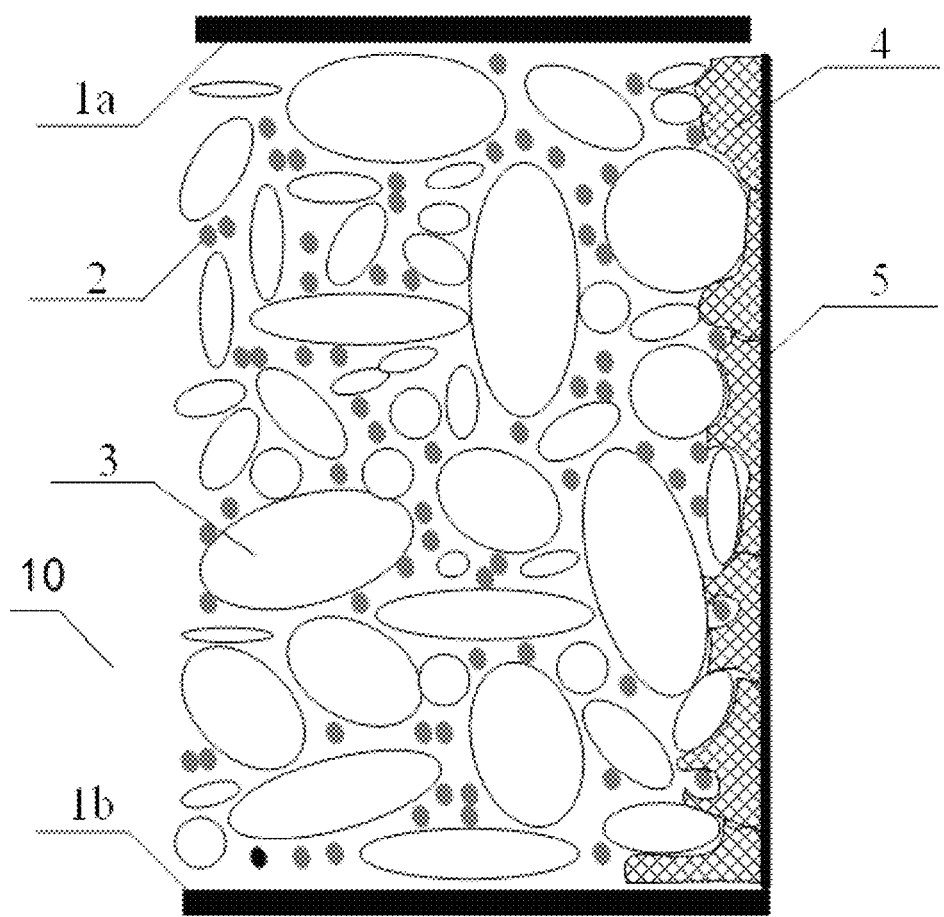
FIG. 5 is a schematic diagram of the specimen preparation method for eliminating a membrane penetration effect on a highly-weathered rock after surface smoothing according to the invention.
Figure 6:
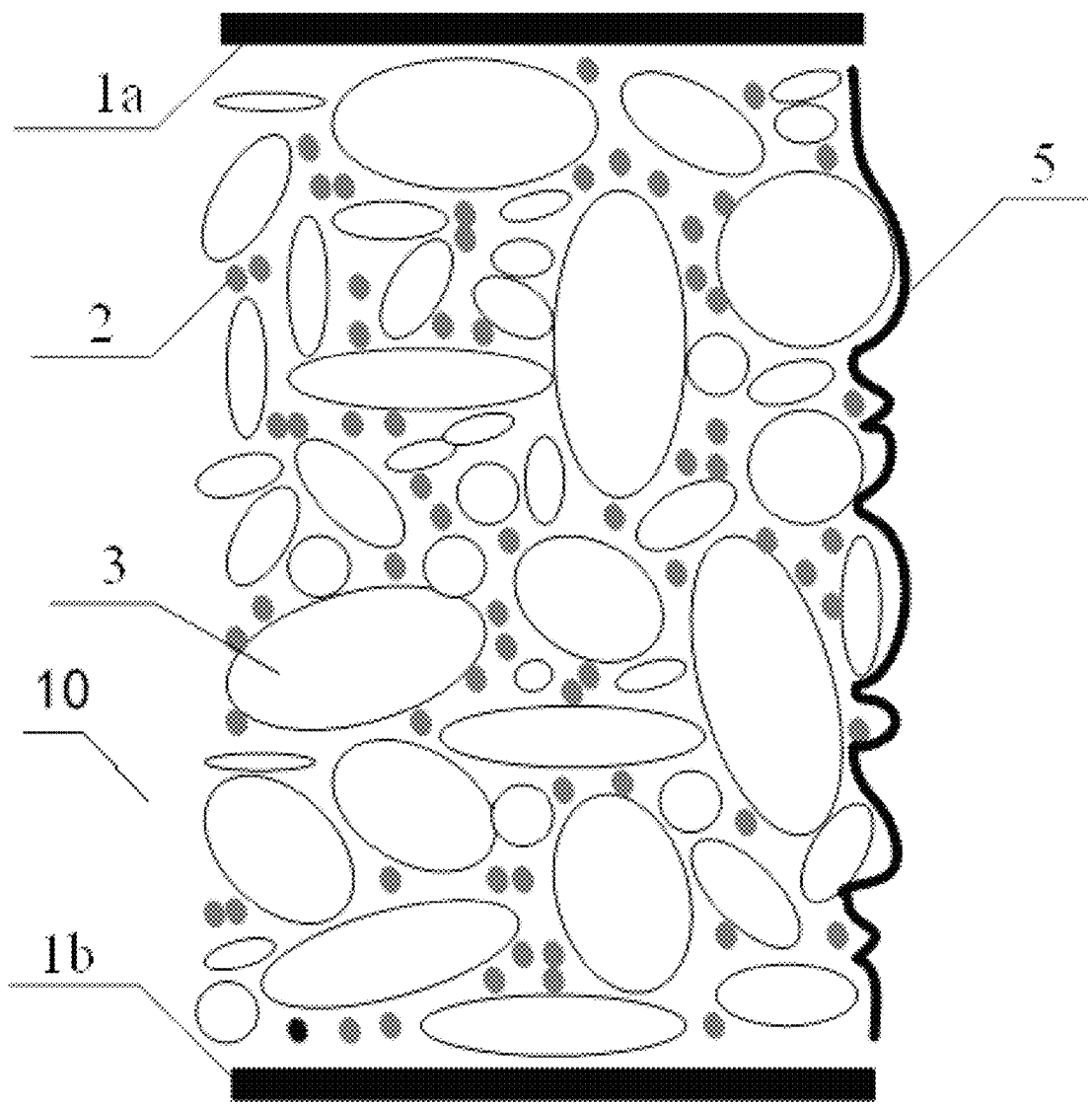
FIG. 6 is a schematic diagram of an undisturbed specimen with the membrane penetration effect not eliminated.
Figure 7:
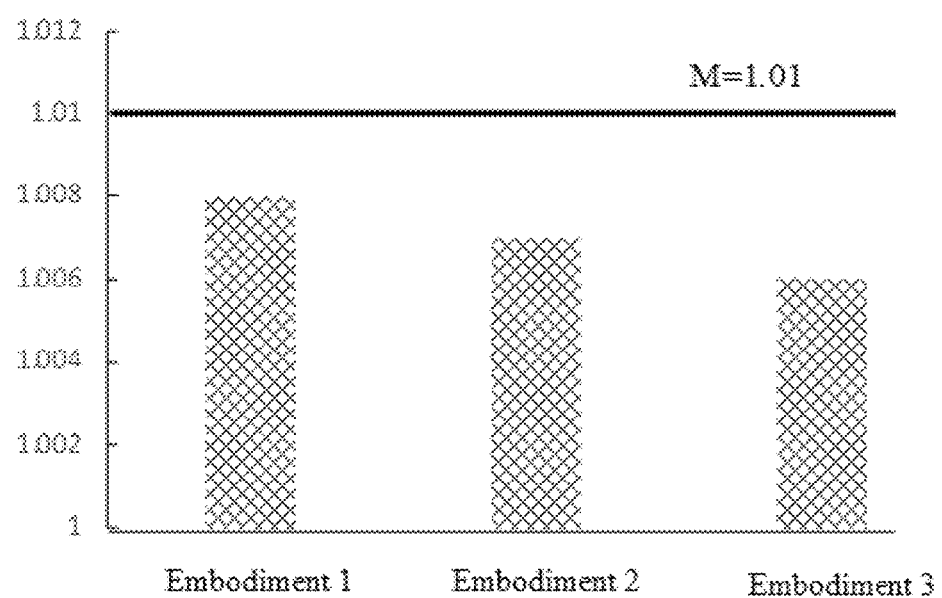
FIG. 7 is a histogram of M values obtained according to three embodiments of the specimen preparation method for eliminating a membrane penetration effect on a highly-weathered rock according to the invention, in which the M values are shown by the longitudinal axis.

As shown in FIG. 6, if the specimen preparation method for eliminating a membrane penetration effect is not adopted, the membrane will penetrate into the specimen. A specimen prepared by the specimen preparation method for eliminating a membrane penetration effect on a highly-weathered rock has a smooth surface, and an obvious membrane penetration effect is avoided (FIG. 5). As can be seen from FIG. 7 which shows M values obtained in Example 1 and Example 2 of the specimen preparation method for eliminating a membrane penetration effect on a highly-weathered rock and in Comparative Test 1, the M values are less than 1.01, which meets the regulations on the membrane thickness in the Standard for Soil Test Method (GB/T50123-1999).

Figure 8:
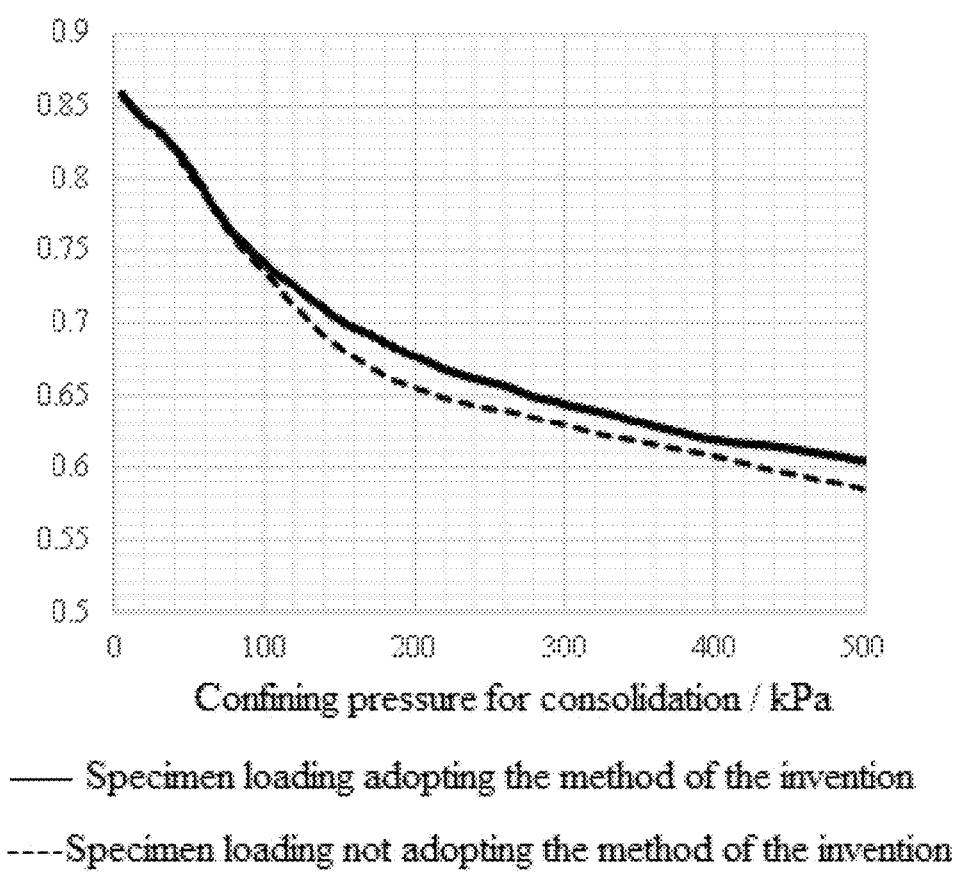
FIG. 8 shows a triaxial shear test result obtained in Embodiment 1 of the specimen preparation method for eliminating a membrane penetration effect on a highly-weathered rock according to the invention, in which the longitudinal axis shows the void ratio e.
Figure 9:
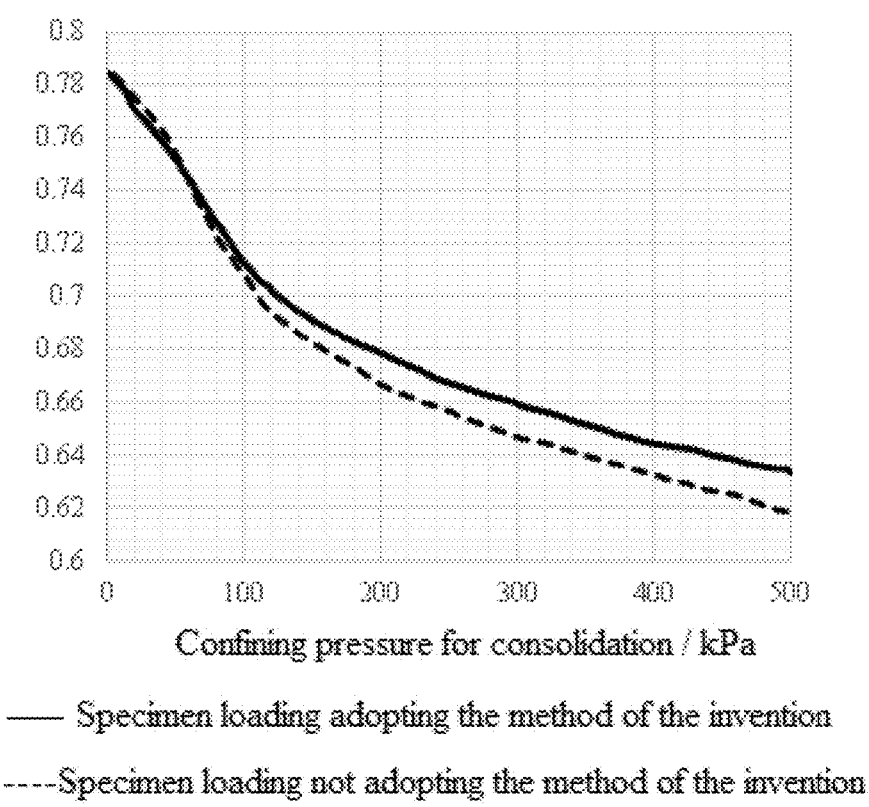
FIG. 9 is a shows a triaxial shear test result obtained in Embodiment 2 of the specimen preparation method for eliminating a membrane penetration effect on a highly-weathered rock according to the invention, in which the longitudinal axis shows the void ratio e.
Figure 10:
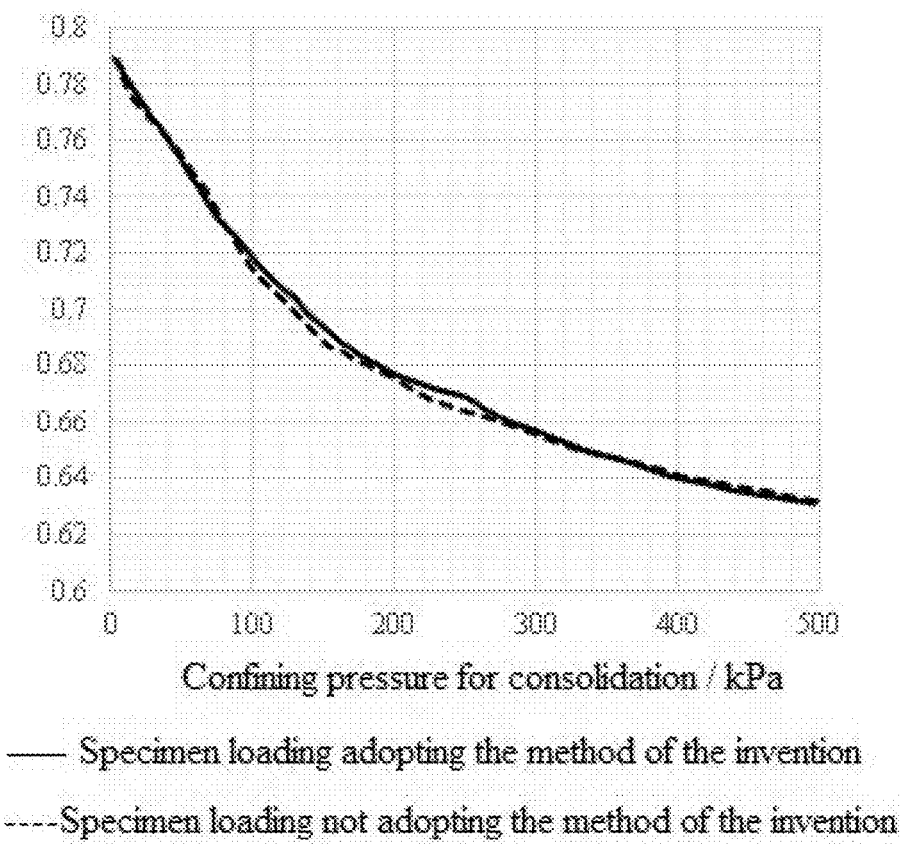
FIG. 10 is a shows a triaxial shear test result obtained in Contrast Test 1 of the specimen preparation method for eliminating a membrane penetration effect on a highly-weathered rock according to the invention, in which the longitudinal axis shows the void ratio e.
Figure 11:
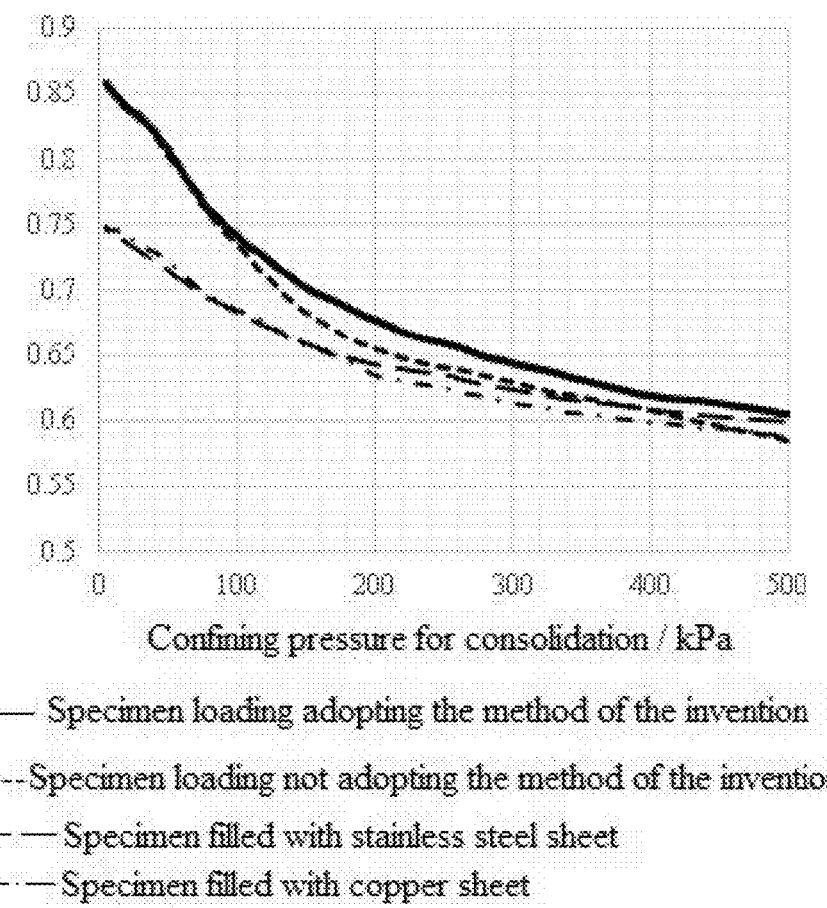
FIG. 11 is shows a triaxial shear test result obtained in Embodiment 1 of the specimen preparation method for eliminating a membrane penetration effect on a highly-weathered rock according to the invention and a triaxial shear test results obtained by filling the surface of a specimen with a stainless steel sheet and a copper sheet respectively, in which the longitudinal axis shows the void ratio e.

In addition, according to triaxial test results obtained in Example 1 and Example 2 of the specimen preparation method for eliminating a membrane penetration effect on a highly-weathered rock (FIGS. 8 and 9), if specimen loading is carried out without the specimen preparation method for eliminating a membrane penetration effect, voids of the specimen are obviously smaller in the consolidation process (the void ratio is typically used as a parameter for evaluating the void size of soil and is defined as the ratio of the void size of soil to solid particles in the soil, and the more obvious the membrane penetration effect, the smaller the void ratio obtained), which indicates that the membrane penetration will reduce the voids and make a measured value of the strength of the highly-weather rock higher, and the membrane penetration effect will become more obvious with the increase of the confining pressure. Moreover, as can be seen from the test results of Example 1 and Comparative Test 2 (the specimen is filled with the stainless steel sheet or the copper sheet in the prior art), the test result obtained by filling the specimen with the stainless steel sheet is basically identical with the test result obtained by filling the specimen with the copper sheet. However, at the initial stage of the test (when a small consolidation pressure is applied), due to the fact that the stainless steel sheet and the copper sheet are rigid fillers which may increase the diameter of the specimen, the void ratio of the specimen is smaller than the void ratio of the specimen prepared according to the technical solution of the invention; and meanwhile, with the increase of the consolidation pressure, the void ratio is still smaller than the void ratio of the specimen obtained according to the technical solution of the invention, which indicates that the technical solution of filling the specimen with the stainless steel sheet or the copper sheet cannot fundamentally eliminate the membrane penetration effect. It can be known from the comparative tests that although the M value obtained in Comparative Test 1 is less than 1.01, which meets the regulations on the membrane thickness in the Standard for Soil Test Method (GB/T50123-1999), the short curing time of the liquid latex 4 and the small thickness of the liquid latex 4 smeared in the membrane 5 in the surface smoothing process in Step (3) make the liquid latex 4 not completely cured and fail to fully fill in the voids during the test, so the membrane penetration effect is not eliminated, and the two curves in FIG. 10 almost coincide. As can be seen, the curing time of the liquid latex 4 and the thickness of the liquid latex 4 smeared in the membrane 5 in Example 1 and Example 2 are optimum, that is, the curing time of the liquid latex 4 and the thickness of the smeared liquid latex 4 in Step (2), Step (3) and Step (4) in this application are optimum.

The technical solution of the invention can effectively eliminate disadvantageous influences of a membrane penetration effect on a highly-weathered rock, such that an obtained triaxial shear test result is true, reliable and precise. The method is featured by non-toxic test materials, low costs, feasible steps, simple operations, and a short test period. The technical solution can avoid the problem of test failures caused when protruding quartz particles on the surface of a specimen penetrate through a membrane under high pressure.

The above examples are merely preferred ones of the invention, and are not intended to limit the invention. Any simple modifications, changes and equivalent structural transformations made to the above examples based on the principle of the invention should also fall within the protection scope of the technical solution of the invention.

What is claimed is:

1. A specimen preparation method, comprising:
   (1) taking a soil specimen out of a soil specimen tube or a packaging bag, removing a soil layer on a surface of the soil specimen by cutting to obtain a standard cylindrical triaxial specimen, and testing a diameter of the specimen with a slide caliper and recording the diameter as $d_1$;
   (2) laying a wet filter paper on upper and lower surfaces of the specimen, smearing a liquid latex on a peripheral surface of the specimen for packaging and leveling with a cutter to make the peripheral surface of the specimen smooth, and placing the packaged specimen in a moisture preservation vat and letting it stand until the liquid latex on the peripheral surface of the specimen is cured;
   (3) disposing a membrane tube around a membrane, turning two ends of the membrane outwards to be attached to an outside of the membrane tube and the portions located outside the membrane tube of the membrane are banded with rubber bands;
   inserting a pointed end of a plastic suction bulb into a suction hole of the membrane tube, and pressing the plastic suction bulb to exhaust air between the membrane and the membrane tube; and
   dipping the liquid latex with a finger wearing a latex glove into the liquid latex and smearing in the membrane, wherein an average thickness of the liquid latex smeared in the membrane is 0.1 mm;
   (4) placing the specimen processed in step (2) into the membrane sleeve prepared in step (3) and integrally curing with the membrane sleeve, wherein an inner surface of the membrane sleeve is coated with the liquid latex, and a thickness of the membrane sleeve is $d_0$;
   (5) instantly placing the specimen processed in step (4) in a triaxial confining pressure chamber after porous stones are placed in an upper portion and a lower portion of the specimen, respectively, applying a confining pressure to press the liquid latex into the specimen, and letting the specimen stand until the liquid latex is cured, wherein the confining pressure is 10 kPa; and (6) releasing the confining pressure, removing the membrane sleeve, measuring an outer diameter $d_2$ of the specimen with a slide caliper, and loading a specimen meeting $d_2/d_1<1.01$ for a triaxial shear test.

2. The specimen preparation method according to claim 1, wherein the diameter of the specimen is 50.00 mm, a height of the specimen is 100.0 mm, the soil specimen contains 15.0 wt % of gravel particles, 50.0 wt % of sand particles and 35.0 wt % of clay particles in step (1); and a thickness of the liquid latex smeared in the membrane is 0.1 mm during step (3).

3. The specimen preparation method according to claim 1, wherein the liquid latex stands in the moisture preservation vat for 5 hrs to be cured during step (2).

4. The specimen preparation method according to claim 1, wherein the liquid latex stands in the confining pressure chamber for 5 hrs to be cured during step (4).

\* \* \* \* \*